United States Patent
Boehm

(10) Patent No.: US 10,506,695 B2
(45) Date of Patent: Dec. 10, 2019

(54) ADAPTIVE STATE OF CHARGE FOR PORTABLE X-RAY DEVICE

(71) Applicant: General Electric Company, Schenectady, NY (US)

(72) Inventor: Manfred David Boehm, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 263 days.

(21) Appl. No.: 15/721,622

(22) Filed: Sep. 29, 2017

(65) Prior Publication Data
US 2019/0104603 A1    Apr. 4, 2019

(51) Int. Cl.
*H05G 1/32* (2006.01)
*A61B 6/00* (2006.01)

(52) U.S. Cl.
CPC ............ *H05G 1/32* (2013.01); *A61B 6/4405* (2013.01); *A61B 6/56* (2013.01)

(58) Field of Classification Search
CPC ................................ G06F 1/3203; H05G 1/32
See application file for complete search history.

(56) References Cited

U.S. PATENT DOCUMENTS

| 5,594,345 A * | 1/1997 | Boehm ............... A61B 6/4405 320/132 |
| 5,867,561 A * | 2/1999 | Strasser .............. A61B 6/4405 378/101 |
| 2005/0028014 A1* | 2/2005 | Allred ..................... H02J 3/14 713/300 |
| 2013/0279661 A1* | 10/2013 | Tamura .................... H05G 1/56 378/98 |
| 2017/0027537 A1* | 2/2017 | Zhang ..................... H05G 1/12 |
| 2018/0014396 A1* | 1/2018 | Imamura ............... H05G 1/265 |

* cited by examiner

*Primary Examiner* — Yara B Green
(74) *Attorney, Agent, or Firm* — McCoy Russell LLP

(57) ABSTRACT

Methods and systems are provided for an adaptive state-of-charge for a portable imaging system. In one embodiment, a method comprises controlling an x-ray source to generate an x-ray exposure, measuring a voltage of a power supply coupled to the x-ray source during the x-ray exposure, and adjusting an available capacity of the power supply based on the voltage. In this way, the full capacity of a power supply may be utilized while compensating for aging of the power supply.

20 Claims, 5 Drawing Sheets

ADAPTIVE STATE OF CHARGE FOR PORTABLE X-RAY DEVICE

FIELD

Embodiments of the subject matter disclosed herein relate to imaging systems, and more particularly, to a rechargeable version of such systems.

BACKGROUND

Imaging systems are widely employed in medical environments, such as hospitals. For example, x-ray systems generally are based upon generation of x-rays that are directed toward a subject of interest. The x-rays traverse the subject and impact a film or a digital detector. To provide greater versatility, some detectors are configured as portable devices, in contrast to others that are fixed at a particular location, such as a table or wall stand. Such portable systems may include a battery for powering the system and thereby enabling full portability.

BRIEF DESCRIPTION

In one embodiment, a method comprises controlling an x-ray source to generate an x-ray exposure, measuring a voltage of a power supply coupled to the x-ray source during the x-ray exposure, and adjusting an available capacity of the power supply based on the voltage. In this way, the full capacity of a battery may be utilized while compensating for aging of the battery.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
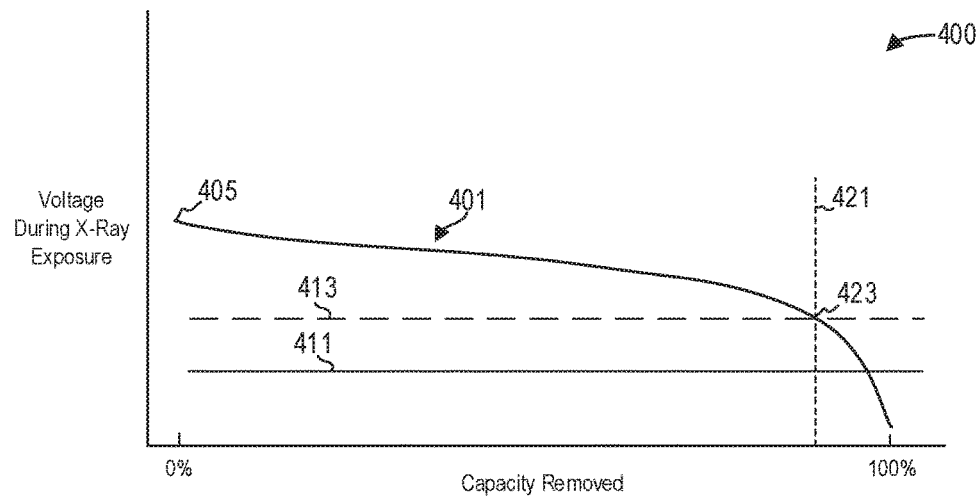
FIG. 4 shows a graph illustrating an example relationship between voltage usage during an x-ray exposure as a function of battery capacity for a new battery.
Figure 5:
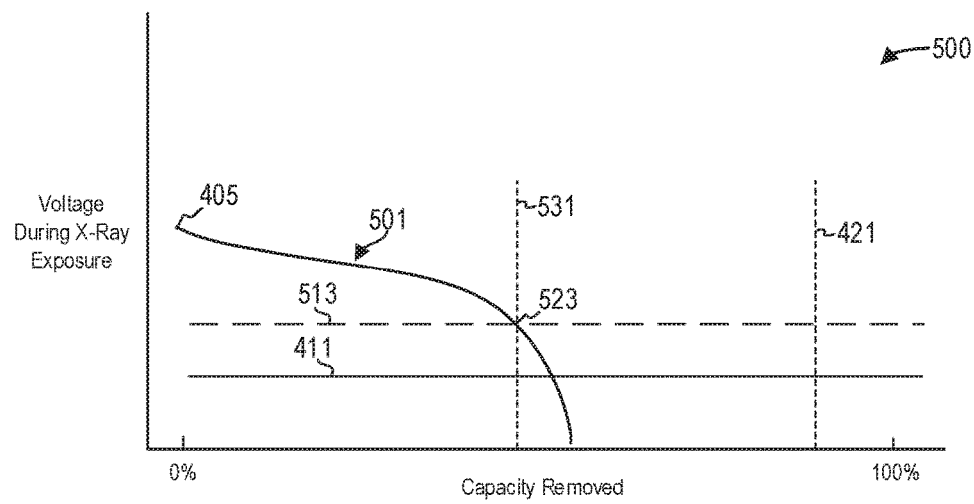
FIG. 5 shows a graph illustrating an example relationship between voltage usage during an x-ray exposure as a function of battery capacity for a battery at the end-of-usable life.
Figure 6:
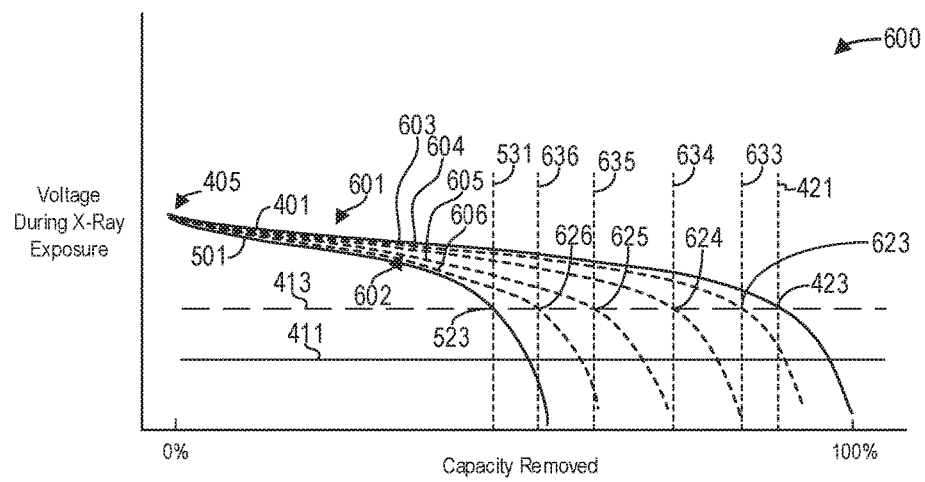
FIG. 6 shows a graph illustrating how battery capacity may decrease over the lifetime of a battery.
Figure 7:
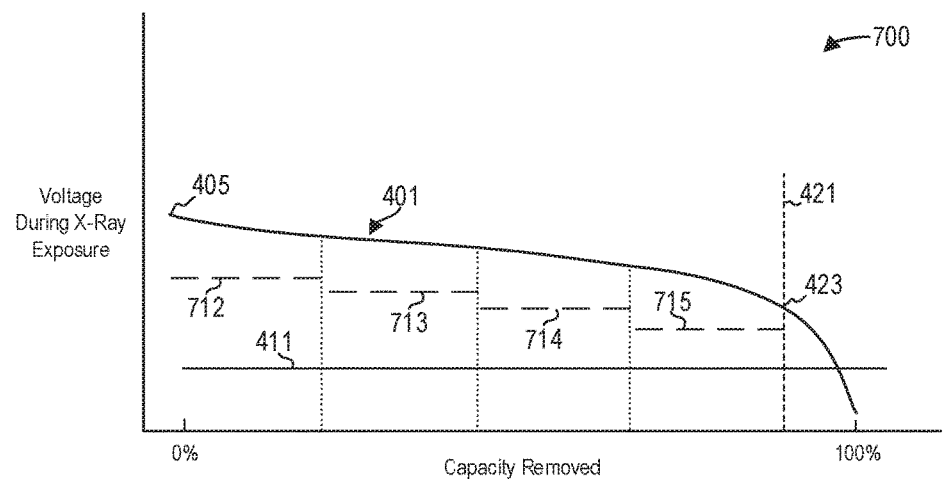
FIG. 7 shows a graph illustrating how battery capacity may be adjusted based on various voltage thresholds.

The following description relates to various embodiments of portable imaging systems. In particular, systems and methods are provided for an adaptive state-of-charge for a portable imaging system. A portable imaging system, such as the portable x-ray system depicted in FIGS. 1 and 2, may include an x-ray device powered by a rechargeable power supply, such as a battery. A method for adjusting the available capacity of the rechargeable power supply, such as the method depicted in FIG. 3, may include reducing the available capacity when a voltage measured during an x-ray exposure is below a threshold. The available capacity may be steadily decreased as the power supply ages, as depicted in FIGS. 4-6. A plurality of thresholds that depend on the state-of-charge of the power supply may be used to adjust the available capacity, as depicted in FIG. 7.

Figure 1:
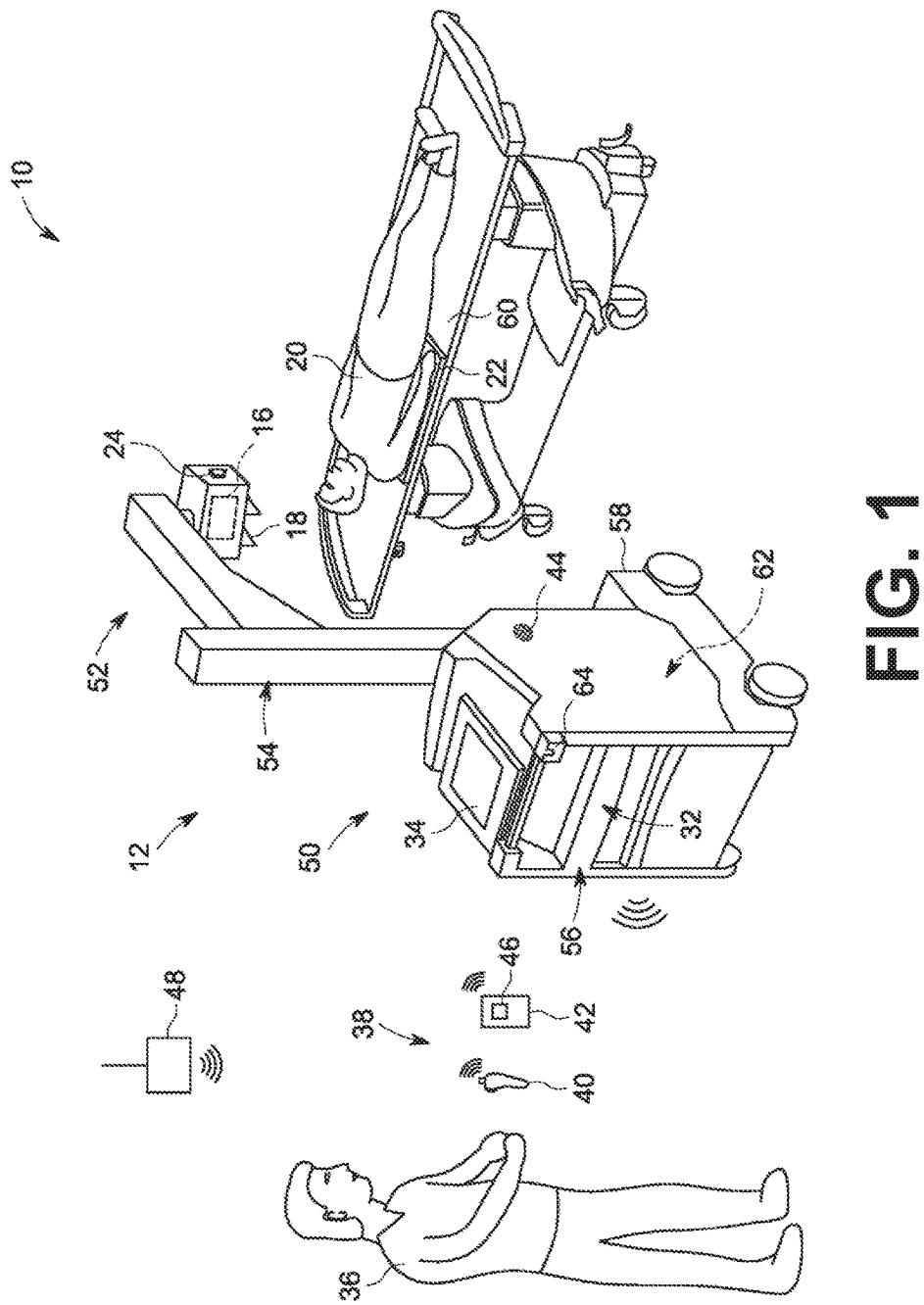
FIG. 1 shows a perspective view of a mobile x-ray system according to an embodiment.

Referring generally to FIG. 1, an x-ray system is represented, referenced generally by reference numeral 10. In the illustrated embodiment, the x-ray system 10 may be a digital or analog x-ray system. The x-ray system 10 is designed both to acquire original images or image data and to process the image data for display (in a digital x-ray system).

In the embodiment illustrated in FIG. 1, the x-ray system 10 includes an imaging system 12. Specifically, the imaging system 12 comprises a mobile imaging system that may be moved to a patient recovery room, an emergency room, a surgical room, or any other space to enable imaging of a patient 20 without requiring transport of the patient 20 to a dedicated (i.e., fixed) x-ray imaging room. The imaging system 12 includes a mobile x-ray base station 50 and image receptor 22. In one embodiment, a support arm 52 may be vertically moved along a support column 54 to facilitate positioning of a radiation source 16 (also referred to herein interchangeably as x-ray tube 16, x-ray radiation source 16, and source 16) and a collimator 18 with respect to the patient 20 and the image receptor 22. In analog x-ray systems 10, the image receptor 22 may include a radiographic film and cassette, phosphorescent screen and computed radiography cassette, or other device. In digital x-ray systems, the image receptor 22 may include a digital x-ray detector.

Further, one or both of the support arm 52 and support column 54 may also be configured to allow rotation of the radiation source 16 about an axis. The x-ray base station 50 may also include camera 24 to assist in positioning of the radiation source 16 and collimator 18, as well as speaker 44 to transmit patient-audible commands. In addition, the x-ray base station 50 may include a speaker located either on a base unit 56, the column 54, or the arm 52, or another location of the x-ray base station 50. Further, the x-ray base station 50 has a wheeled base 58 for movement of the station 50.

The patient may be located on a bed 60 (or gurney, table, or any other support) between the x-ray source 16 and the image receptor 22 and subjected to x-rays that pass through the patient 20 and are received either by a film, phosphorescent screen, or other medium. During an imaging sequence using the digital x-ray system 10, the image receptor 22, also referred to herein as detector 22, receives x-rays that pass through the patient 20 and transmits imaging data to a base unit 56. The detector 22 is in communication with the base unit 56. The base unit 56 houses systems electronic circuitry 62 that acquires image data from the detector 22 and that, where properly equipped, may process the data to form desired images. In addition, the systems electronic circuitry 62 both provides and controls power to the x-ray source 16 and the wheeled base 58 in either the digital or analog x-ray system 10.

Also depicted in FIG. 1, the imaging system 12 includes a workstation 32 and display 34. More specifically, the base unit 56 has the operator workstation 32 and display 34 that enables the user 36 to operate the x-ray system 10. In one embodiment, the workstation 32 may include or provide the functionality of the imaging system 12 such that a user 36, by interacting with the workstation 32 may control operation of the source 16 and detector 22 (in a digital x-ray system 10). The operator workstation 32 may include buttons, switches, or the like to facilitate operation of the x-ray source 16 and detector 22.

In other embodiments, the functions of the imaging system 12 may be decentralized, such that some functions of the imaging system 12 are performed at the workstation 32, while other functions are performed by another component of the x-ray system 10, such as a handheld interface device 38. The handheld interface device 38 is configured to be held by a user 36 and to communicate wirelessly with the imaging system 12. The handheld interface device 38 is also configured to prepare the imaging system 12 for an exposure and to initiate an exposure. The imaging system 12 is configured to wirelessly communicate system operational data to the handheld interface device 38 and the handheld interface device 38 is configured to provide a user-detectable indication of the operational status based on the data. In one embodiment, handheld interface device 38 (e.g., 40) is simply designed to prepare and initiate an exposure, as well as to receive system operational data and to provide an indication of the data. It is noted that the imaging system 12 and handheld interface device 38 may utilize any suitable wireless communication protocol, such as an IEEE 802.15.4 protocol, an ultra-wideband (UWB) communication standard, a Bluetooth communication standard, or any IEEE 802.11 communication standard.

In another embodiment, the handheld interface device 38 (e.g., 42) is configured to receive a user-input command for operation of the imaging system 12 (e.g., changing x-ray source settings or moving the x-ray base station 50) prior to initiation of an x-ray exposure sequence and to wirelessly transmit the command to the imaging system 12. For example, the imaging system 12 may include a speaker 44 to transmit patient-audible commands to the patient 20 in response to a signal from the handheld interface device 42. The speaker 44 may be located on the operator workstation 34, near the radiation source 16, in the table 60, or another location. In response to wirelessly receiving the command from the handheld interface device 42, the imaging system 12 executes the command. Also, the handheld interface device 42 includes a user-viewable screen 46 and is configured to receive and display patient data on the screen 46. The imaging system 12 is configured to communicate patient data or instructions to the handheld interface device 42. In one embodiment, the workstation 32 may be configured to function as a server of instructions and/or content on a network 48 of the medical facility, such as a hospital information system (HIS), a radiology information system (RIS), and/or picture archiving communication system (PACS), and to provide these instructions and/or content to the handheld interface device 42. Alternatively, the network 48 may wirelessly communicate directly with the handheld interface device 42.

The x-ray base station 50 has a holder or cradle 64 for the handheld interface device 38 when the device 38 is not in use. The cradle 64 may be configured to recharge the battery of the handheld interface 38, either through conductive charge contacts or with a contactless method such as inductive or capacitive charging.

Figure 2:
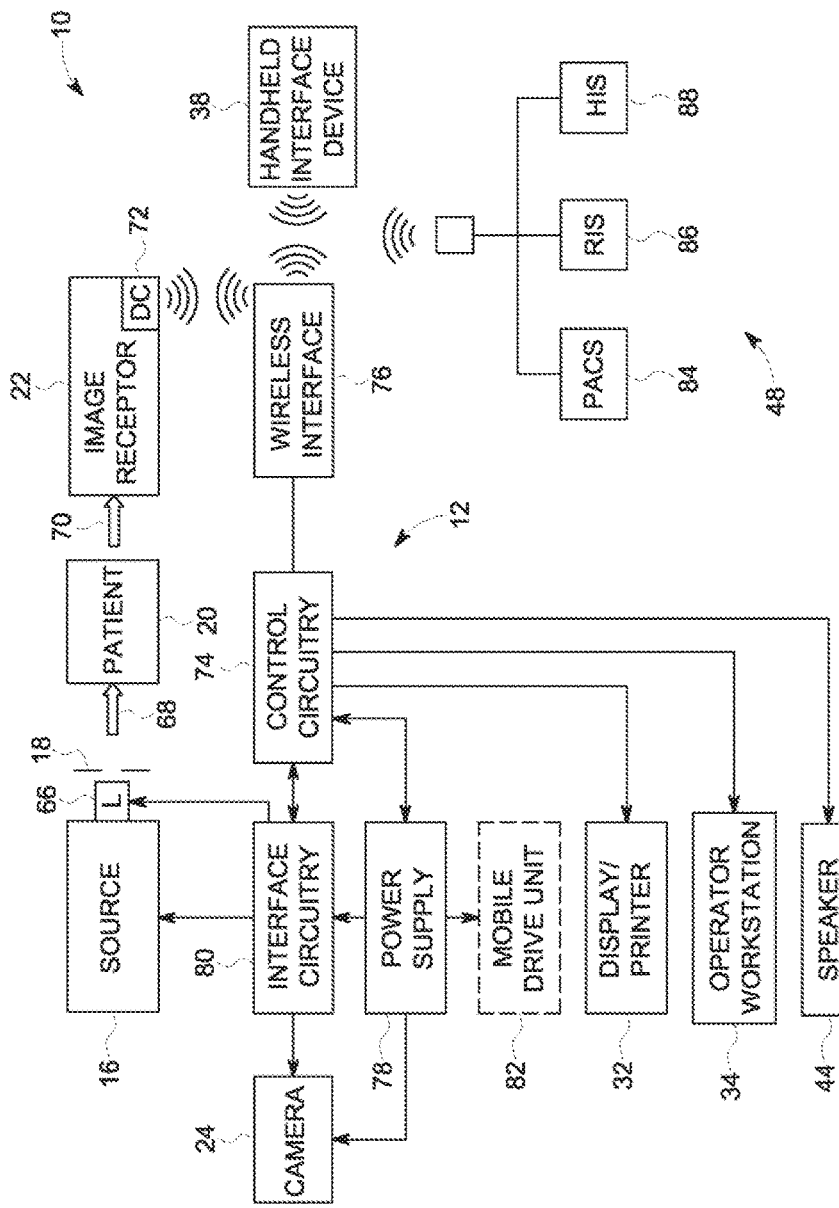
FIG. 2 shows a diagrammatical overview of the mobile x-ray system of FIG. 1.

FIG. 2 illustrates diagrammatically the x-ray system 10 described in FIG. 1, in particular, digital x-ray system 10, although some of the below description applies to analog x-ray systems 10 as well. As illustrated in FIG. 2, the x-ray system 10 includes the source of x-ray radiation 16 positioned adjacent to the collimator 18. A light source 66, also known as a collimator light, is positioned between the x-ray source 16 and the collimator 18. The collimator 18 permits a stream of radiation 68 or light to be directed to a specific region in which an object or subject, such as the patient 20, is positioned. A portion 70 of the radiation passes through the subject and impacts the image receptor or digital x-ray detector 22. As will be appreciated by those skilled in the art, the detector 22 in digital x-ray system 10 converts the x-ray photons received on its surface to lower energy photons, and subsequently to electric signals, which are acquired and processed to reconstruct an image of the features within the subject. The collimator light 66 in the collimator 18 directs light onto the same area where the x-ray photons will pass and can be used to position the patient 20 before exposure. The collimator light 66 can be turned on and off with a user input on the imaging system 12 or on the handheld interface device 38.

Moreover, in digital x-ray systems, the detector 22 is coupled to a detector controller 72 which commands acquisition of the signals generated in the detector 22. The detector controller 26 may also execute various signal processing and filtration functions, such as for initial adjustment of dynamic ranges, interleaving of digital image data, and so forth. The detector controller 26 is responsive to signals from control circuitry 74 communicated wirelessly via a wireless interface 76. In general, the control circuitry 74 commands operation of the imaging system 12 to execute examination protocols and to process acquired image data (in digital x-ray systems 10). In the present context, the control circuitry 74 also includes signal processing circuitry, typically based upon a programmed general purpose or application-specific digital computer, and associated devices, such as optimal memory devices, magnetic memory devices, or solid-state memory devices, for storing programs and routines executed by a processor of the computer to carry out various functionalities, as well as for storing configuration parameters and image data; interface circuits; and so forth.

In both digital and analog x-ray systems 10, the radiation source 16 is controlled by the control circuitry 74 which controls signals for examination sequences. For example, the control circuitry 74 can inhibit the operation of the radiation source 16 if the correct examination conditions are not in place. In addition, the control circuitry 74 controls a power supply 78 which supplies power to the radiation source 16, light source 66, camera 24, as well as the control circuitry 74. Interface circuitry 80 facilitates the provision of power to the radiation source 16, light source 66, camera 24, and control circuitry 74. The power supply 78 also provides power to a mobile drive unit 82 to drive the movement of the wheeled base 58 of the x-ray base station 50. The power supply 78 may comprise one or more batteries. For example, the power supply 78 may comprise one or more lead-acid batteries.

The control circuitry 74 is linked to at least one output device, such as a display or printer 34. The output device may include standard or special purpose computer monitors and associated processing circuitry. One or more operator workstations 34 may be further linked in the system for outputting system parameters, requesting examinations, viewing images (in digital x-ray systems 10), and so forth. In general, displays, printers, workstations, and similar devices supplied within the system may be local to the imaging components, or may be remote from these components, such as elsewhere within an institution or hospital, or in an entirely different location, linked to the imaging system 12 via one or more configurable networks, such as the Internet, virtual private networks, and so forth. The control circuitry 74 may also be linked to the speaker 44 which provides audible signals such as locator signals or patient-audible commands.

The imaging system 12 communicates wirelessly with the handheld interface device 38 via the wireless interface 76. The control circuitry 74 provides the handheld interface 38 system operational data (e.g., inhibit the operation of radiation source), images reconstructed from image data from the detector 22, images of the patient generated by the camera 24, and patient data, as well as other information. The handheld interface device 38 wirelessly communicates a signal to prepare for and initiate an exposure and other commands for operation of the imaging system 12, as well as the location and/or movement of the device 12 relative to the system 12. Besides receiving patient data and/or instructions from the imaging system 12, the handheld interface device 38 wirelessly receives patient information and/or instructions (e.g., imaging sequences to be performed) from the medical facility's network 48. The medical facility network 48 includes PACS 84, RIS 86, and/or HIS 88 to provide the information and/or instructions. The network 48 may also communicate the patient information and/or instructions to imaging system 12, which may then provide the information and/or instructions to the handheld interface device 38.

Although a portable imaging system is depicted in FIGS. 1 and 2, it should be appreciated that in some examples, the imaging system 12 may be a stationary system disposed in a fixed x-ray imaging room. Further, the imaging system 12 may comprise a portable imaging system, though one of ordinary skill in the art should appreciated that in some examples the portability of the imaging system 12 may configured differently than the mobile x-ray base station 50 depicted in FIG. 1.

Figure 3:
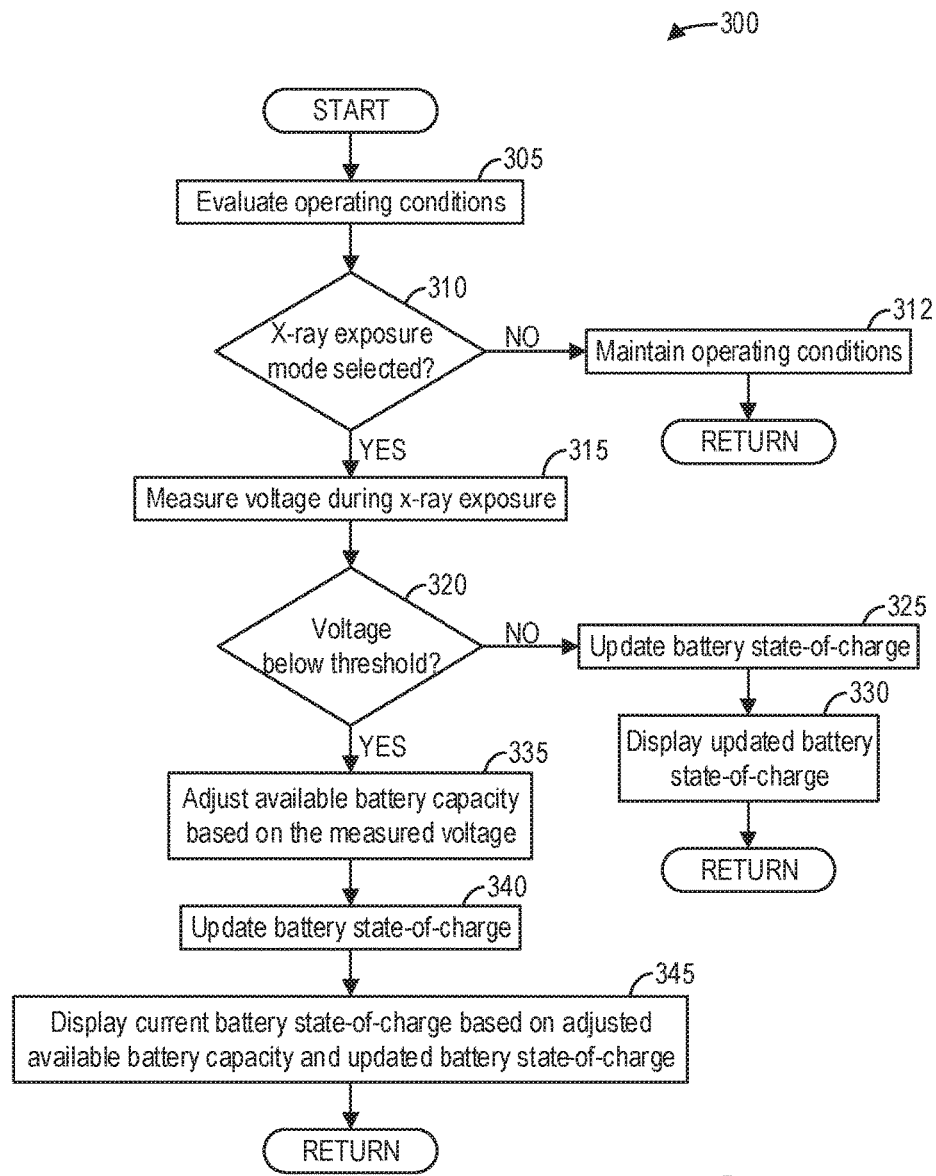
FIG. 3 shows a high-level flow chart illustrating an example method for determining a battery state-of-charge according to an embodiment.

FIG. 3 shows a high-level flow chart illustrating an example method 300 for determining a battery state-of-charge for a portable x-ray device according to an embodiment. In particular, method 300 relates to adjusting a battery capacity based on voltage usage during an x-ray exposure. Method 300 may be described with respect to the systems and components of FIGS. 1 and 2, though it should be appreciated that the method may be implemented with other systems and components without departing from the scope of the present disclosure. Method 300 may be implemented as executable instructions in non-transitory memory, for example in the control circuitry 74. Furthermore, the terms "battery," "power supply" "rechargeable power supply," and "power source" may be used interchangeably herein.

Method 300 begins at 305. At 305, method 300 evaluates operating conditions. Operating conditions may include, but are not limited to, an operating mode of the x-ray device, current draw of the power supply, voltage draw of the power supply, ampere hours remaining of the power supply, current state of charge of the power supply, available capacity of the power supply, and so on. Evaluating such operating conditions may comprise measuring such conditions, as a non-limiting example.

At 310, method 300 determines if an x-ray exposure mode is selected. For example, the portable x-ray device or imaging system may include several operating modes, such as an idle mode, a power-assisted motion mode, and an x-ray exposure mode. The operating modes may correspond to different current loads on the power source. For example, the idle mode may comprise a low current load mode, the power-assisted motion mode may comprise a moderate current load mode, and the x-ray exposure mode may comprise a high current load mode. Of these modes, the x-ray exposure mode or high current load mode subjects the power source to the most strenuous demands with current draws 50 to 100 times higher than the other operating modes. As discussed further herein, the method may only update the available capacity of the power source in response to an x-ray exposure mode. It should be appreciated that the available capacity may be updated during the x-ray exposure mode, immediately after performing an x-ray exposure, a predetermine duration after performing an x-ray exposure, and so on. Further, the term "available capacity" as used herein refers to the total amount of actual capacity (or energy) that may be available prior to the system preventing further x-rays or 0% charge indication.

If an x-ray exposure mode is not selected ("NO"), method 300 proceeds to 312. At 312, method 300 maintains operating conditions. In other words, the imaging system continues to function in accordance with other routines or operating modes of the system. In this way, the method does not attempt to adjust the available capacity when the imaging system does not operate in an x-ray exposure mode. It should be appreciated that the imaging system continuously tracks and updates the state-of-charge of the power source during operational modes other than the x-ray exposure mode. Method 300 then returns.

If an x-ray exposure mode is selected ("YES"), method 300 proceeds to 315. At 315, method 300 measures the voltage of the power source during an x-ray exposure. At 320, method 300 determines if the voltage measured at 315 is below a threshold. As discussed further herein with regard to FIG. 4, in some examples, the threshold may be selected to provide a buffer above an error-free threshold. In some examples, the threshold may be based on the current available capacity. For example, the threshold may be higher or lower depending on the current available capacity. Furthermore, the threshold may be based on the currently-indicated state-of-charge of the power source. Thresholds based on a currently-indicated state-of-charge of the power source are described further herein with regard to FIG. 7.

If the voltage is not below the threshold ("NO"), method 300 proceeds to 325. At 325, method 300 updates the state-of-charge of the power source. For example, the method may update the current state-of-charge of the power source using a technique such as current integration. The updated state-of-charge may be expressed as a percentage of the current available capacity. At 330, method 300 may display the updated battery state-of-charge. It should be appreciated that the updated battery state-of-charge displayed to the user may not comprise a specific state-of-charge, and that instead the specific state-of-charge may be tracked internally. In some examples, a general indication of the state-of-charge of the power source may be displayed to the user. As an illustrative but non-limiting example, a green/yellow/red indicator may be utilized where green indicates a substantial capacity remaining, yellow indicates adequate capacity but suggests charging, and red indicates that the power source should be charged immediately. Thus, a green charge indicator may be displayed when the state-of-charge is above a first state-of-charge threshold, such as 70% of the available capacity, a yellow charge indicator may be displayed when the state-of-charge is above a second state-of-charge threshold, such as 30% of the available capacity, and a red charge indicator may be displayed when the state-of-charge is below the second state-of-charge threshold. It should be appreciated that the state-of-charge thresholds may comprise percentages of the available capacity other than 70% and 30%. Method 300 then returns.

However, referring again to 320, if the voltage is below the threshold ("YES"), method 300 proceeds to 335. At 335, method 300 adjusts the available capacity of the power source based on the voltage measured at 315. More specifically, the method adjusts the available capacity of the power source. In some examples, the available capacity of the power source comprises a percentage of the full rated capacity of the power source. Adjusting the available capacity of the power source comprises decreasing the available capacity used to determine the state-of-charge of the power source. For example, for a new power source, the initial available capacity of the power source may be defined as 80% of the full rated capacity of the power source, thereby providing a 20% margin with respect to the full rated capacity. In other words, for a new fully-charged power source, the method allows the power source to discharge 80% of its full rated capacity before indicating that zero charge is available to the user.

The method may adjust the available capacity of the power source by a predetermined amount. For example, the available capacity of the power source may be decreased by a predetermined percentage of the full rated capacity. The predetermined percentage may comprise a fixed percentage, including but not limited to 1%, 2%, 3%, and so on. It should be appreciated that the fixed percentage may comprise a fractional percentage, such as 0.5%, or a larger percentage, such as 10%, of the full rated capacity.

As another example, the available capacity of the power source may be decreased by a percentage of the full rated capacity, where the percentage is based on the current available capacity. As a non-limiting example, the available capacity may be decreased by a first percentage when the currently available capacity is above a threshold capacity, while the available capacity may be decreased by a second percentage greater than the first percentage when the current available capacity is below the threshold capacity. In this way, the adjustments to the available capacity may become increasingly larger as the power source ages. It should also be appreciated that in some examples, the adjustments to the available capacity may become increasingly smaller as the power source ages.

At 340, method 300 updates the current state-of-charge of the power source. For example, the method may update the current state-of-charge based on current integration measurements and the adjusted available capacity.

At 345, method 300 displays the current state-of-charge of the power source based on the updated available capacity of the power source and the updated state-of-charge of the power source. For example, the method may output the current state-of-charge of the power source, updated at 340 to account for the adjusted available capacity, to the screen 46 of the handheld interface device 42 and/or the display 34 of the imaging system 12. Method 300 then returns.

As an illustrative example, FIG. 4 shows a graph 400 illustrating an example relationship between voltage during an x-ray exposure as a function of power source capacity for a new power source according to an embodiment. In particular, plot 401 illustrates the voltage during an x-ray exposure as a function of the capacity removed from the power source for a new power source.

Voltage 405 may be measured when 0% of the capacity is removed from the power source, or in other words, when the power source is fully charged. As the power source is discharged, the impedance of the battery increases. This impedance has a maximum value above which the x-ray device generates errors or will no longer function. Considering the impedance of the power source in terms of the voltage under load, the error-free threshold 411 indicates the voltage value below which the x-ray device generates errors. In order to provide a buffer above the error-free threshold 411 and therefore prevent the x-ray device from possibly operating under conditions where errors may occur, a buffer threshold 413 may establish a desired margin above the error-free threshold. Furthermore, the initial available capacity 421 may be determined based on the buffer threshold 413, or vice versa. For example, the voltage 423 which equals the buffer threshold 413 may comprise the available capacity 421.

The initial available capacity may be predetermined as a percentage of the full rated capacity of the power source. As an illustrative and non-limiting example, the initial available capacity may be set to 80% of the full rated capacity of the power source. Voltage 423 may be measured when the capacity of the power source comprises the available capacity 421. Thus, if the state-of-charge of the power source indicated to the user is approximately 0%, such that an amount of capacity removed from the power source equals the available capacity 421, then the voltage 423 may be measured during an x-ray exposure.

As the power source ages, the usable capacity of the power source decreases. To illustrate, FIG. 5 shows a graph 500 illustrating an example relationship between voltage during an x-ray exposure as a function of power source capacity for a power source at the end of its usable life according to an embodiment. In particular, plot 501 illustrates the voltage during an x-ray exposure as a function of the capacity removed from the power source for a power source near its end of useful life.

Rather than indicate zero charge when the capacity removed equals the initial available capacity 421, zero charge is indicated when the capacity removed equals the final available capacity 531. In some examples, the final available capacity 531 may comprise a predetermined percentage of the full rated capacity of the power source. The final available capacity 531 may be selected to ensure that the power source provides sufficient voltage during an x-ray exposure, even if the power source is mostly discharged at the end of its useful life, to avoid errors or other system failures. As an illustrative and non-limiting example, the final available capacity 531 may comprise 50% of the full rated capacity of the power source. In other examples, the final available capacity 531 may comprise a percentage greater than or less than 50% of the full rated capacity of the power source.

The buffer threshold 513 may be determined based on the final available capacity 531. For example, as depicted, the buffer threshold 513 comprises the value of the voltage 523 of the power source at the final available capacity 531. In some examples, the buffer threshold 513 may comprise the same value as buffer threshold 413, though it should be appreciated that a different buffer threshold may be used for each indicated state-of-charge. The buffer threshold 513 may comprise the threshold discussed with respect to FIG. 3, such that if the voltage measured at 315 is below the buffer threshold, the method reduces the available capacity of the power source.

If the voltage measured during an x-ray exposure is below the buffer threshold 513 when the available capacity of the power source equals the final available capacity 531, the power source may be considered to be at the end of its useful life. In some examples, the voltage may be measured below the buffer threshold 513 a specified number of times prior to determining that the available capacity 531 should be decreased.

In some examples, upon determining that the power source is at the end of its useful life, the imaging system or portable x-ray device may display a message indicating a need for power source replacement. Additionally or alternatively, the portable x-ray device may disable use of the high current load mode or x-ray exposure mode in order to prevent such operation of the portable x-ray device with the fully-depleted power source.

As described above, FIGS. 4 and 5 depict voltage during an x-ray exposure for a new power source and a depleted power source. For a new power source, the initial available capacity 421 of the power source may be set to a specified first percentage of the full rated capacity of the power source, such as 80%. For a power source approaching the point of requiring replacement or servicing, the final available capacity 531 of the power source may be set to a specified second percentage of the full rated capacity of the power source, wherein the specified second percentage is less than the specified first percentage, such as 50%. A plurality of intermediate capacities may be provided between the initial available capacity 421 and the final available capacity 531.

For example, FIG. 6 shows a graph 600 illustrating how battery capacity may be adjusted over the lifetime of a power source according to an embodiment. Graph 600 includes a plurality of plots 601 illustrating voltage during an x-ray exposure as a function of capacity removed from the power source. Each of the plurality of plots 601 corresponds to a different age of the power source. Specifically, the plurality of plots 601 includes the plot 401 illustrating voltage as a function of capacity removed for a new power source as described hereinabove with regard to FIG. 4, the plot 501 illustrating voltage as a function of capacity removed for a power source at the end of usable life as described hereinabove with regard to FIG. 5, and a plurality of intermediate plots 602 (depicted as dashed curves) that correspond to different ages of the power source and thus are intermediate to plot 401 and plot 501. It should be appreciated that the term "ages" as used herein does not necessarily refer to a calendar age but may instead refer to a usage amount; a lightly-used power source ages more slowly than a heavily-used power source. Graph 600 also depicts the error-free threshold 411 and the buffer threshold 413 described hereinabove with regard to FIG. 4.

As depicted, a full charge is indicated to the user when approximately 0% capacity is removed from the power source. A voltage 405 may be measured for each of the plots 601 when 0% capacity is removed from the power source, though it should be appreciated that in some examples, the voltage measured when 0% capacity is removed may be within a range of voltages around voltage 405.

Zero charge is indicated at different points for each of the plots 601. Specifically, zero charge is indicated to the user when 100% of the available capacity is removed from the power source, which occurs at different points for the different plots 601. For example, zero charge is indicated to the user at 421 for a new power source as depicted by plot 401, while zero charge is indicated to the user at 531 for a power source at the end of usable life as depicted by plot 501.

As discussed hereinabove with regard to FIG. 3, the method 300 adjusts an available capacity of a power source as the power source ages. For example, for a new power source, the plot 401 may illustrate the voltage during an x-ray exposure as a function of the capacity removed from the power source. The available capacity may comprise a percentage of the full rated capacity of the power source, such as 80%, as depicted by the initial available capacity 421, hereinafter also referred to as the first available capacity 421. That is, when the capacity removed from the power source equals the first available capacity, the state-of-charge of the power source is treated as zero. Once a voltage is measured during an x-ray exposure that falls below the buffer threshold 413, the available capacity is decreased, for example, from the first available capacity 421 to the second available capacity 633. For the second available capacity 633, full charge is indicated at 0% capacity removed while zero charge is indicated when the capacity removed equals the second available capacity 633. When the available capacity comprises the second available capacity 633, a voltage 623 may be measured when the power source is nearly completely depleted (e.g., when the second available capacity 633 is removed from the power source).

Once a voltage is measured during an x-ray exposure that falls below the buffer threshold 413 when the available capacity comprises the second available capacity 633, the available capacity may be adjusted or decreased from the second available capacity 633 to the third available capacity 634. For the third available capacity 634, full charge is indicated at 0% capacity removed while zero charge is indicated when the capacity removed equals the available capacity 634. When the available capacity of the power source comprises the third available capacity 634, a voltage 624 may be measured when the power source is nearly completely depleted (e.g., when the capacity removed from the power source is approximately equal to the third available capacity 634)

Once a voltage is measured during an x-ray exposure that falls below the buffer threshold 413 when the available capacity comprises the third available capacity 634, the available capacity may be adjusted or decreased from the third available capacity 634 to the fourth available capacity 635. For the fourth available capacity 635, full charge is indicated at 0% capacity removed while zero charge is indicated when the capacity removed equals the fourth available capacity 635. When the available capacity of the power source comprises the fourth available capacity 635, a voltage 625 may be measured when the power source is nearly completely depleted, as discussed above.

Once a voltage is measured during an x-ray exposure that falls below the buffer threshold 413 when the available capacity comprises the fourth available capacity 635, the available capacity may be adjusted or decreased from the fourth available capacity 635 to the fifth available capacity 636. For the fifth available capacity 636, full charge is indicated at 0% capacity removed while zero charge is indicated when the capacity removed equals the fifth available capacity 636. When the available capacity of the power source comprises the fifth available capacity 636, a voltage 626 may be measured during an x-ray exposure near zero charge.

Finally, once a voltage is measured during an x-ray exposure that falls below the buffer threshold 413 when the available capacity comprises the fifth available capacity 636, the available capacity of the power source may be adjusted or decreased from the fifth available capacity 636 to the sixth available capacity 531, also referred to herein as the final available capacity 531. For the sixth available capacity 531, full charge is indicated at 0% capacity removed while zero charge is indicated when the capacity removed equals the sixth available capacity 531. As discussed hereinabove, when the available capacity of the power source comprises the sixth available capacity 531, a voltage 523 may be measured during an x-ray exposure when the power source is nearly completely discharged.

Although six available capacities are depicted in FIG. 6, it should be appreciated that the number of available capacities is illustrative and non-limiting, and that the method described herein may be implemented with a number of available capacities greater than or less than six. Further, the six available capacities are depicted in FIG. 6 at different intervals; that is, the decrease in available capacity between the first and the second available capacities 421 and 633 is smaller than the decrease in available capacity between the second and third available capacities 633 and 634. Similarly, the decrease in available capacity is depicted as varying between the available capacities 634, 635, 636, and 531. It should be appreciated that in some examples, the adjustments to the available capacity may be a fixed percentage of the full rated capacity, as described hereinabove with regard to FIG. 3, rather than a variable percentage of the full rated capacity. Both the number of available capacities and the decrease in capacity between the available capacities may be predetermined in order to optimize the use of the power source over the lifetime of the power source.

Further, although the examples depicted in FIGS. 4-6 include a single buffer threshold 413 or 513, it should be appreciated that multiple buffer thresholds may be utilized. As an illustrative and non-limiting example, FIG. 7 shows a graph 700 illustrating how available capacity may be adjusted based on various thresholds according to an embodiment. Specifically, graph 700 includes plot 401 illustrating voltage during x-ray exposures as a function of capacity removed from the power source for a new power source.

Rather than a single buffer threshold such as buffer threshold 413, a plurality of buffer thresholds to determine when to adjust the available capacity. Thus, graph 700 depicts a plurality of buffer thresholds including first buffer threshold 712, second buffer threshold 713, third buffer threshold 714, and fourth buffer threshold 715. Each buffer threshold corresponds to a voltage greater than the voltage corresponding to the error-free threshold 411.

As depicted, the available capacity of the power source is divided into multiple ranges with a different buffer threshold for each range. In particular, the first buffer threshold 712 corresponds to a first range of the capacity removed, the second buffer threshold 713 corresponds to a second range of the capacity removed, the third buffer threshold 714 corresponds to a third range of the capacity removed, and the fourth buffer threshold 715 corresponds to a fourth range of the capacity removed. The first range corresponds to a state-of-charge of the power source ranging from 100% to 75%, the second range corresponds to a state-of-charge of the power source ranging from 75% to 50%, the third range corresponds to a state-of-charge of the power source ranging from 50% to 25%, and the fourth range corresponds to a state-of-charge of the power source ranging from 25% to 0%.

Thus, the first buffer threshold 712 comprises the minimum voltage allowed when the state-of-charge of the power source ranges from 100% to 75%, the second buffer threshold 713 comprises the minimum voltage allowed when the state-of-charge of the power source ranges from 75% to 50%, the third buffer threshold 714 comprises the minimum voltage allowed when the state-of-charge of the power source ranges from 50% to 25%, and the fourth buffer threshold 715 comprises the minimum voltage allowed when the state-of-charge of the power source ranges from 25% to 0%.

Although four ranges are depicted, it should be appreciated that the number of ranges could be as few as a single range (such that a single buffer threshold is used, e.g., buffer threshold 413) or may be extended to a continuous range where the minimum allowed voltage is a function of the state-of-charge of the power source.

Thus, as the power source ages, the power source will start to approach the buffer thresholds for each range. Generally, the rate of approach is faster for a lower state-of-charge than a higher state-of-charge. When any buffer threshold is exceeded, the available capacity is adjusted (i.e., decreased). By providing different buffer thresholds that depend on the state-of-charge, the aging of the power source may be compensated even if the user only operates the imaging system in one or two of the ranges. For example, if a user generally keeps the power source fully or mostly charged (e.g., the power source is regularly recharged such that the state-of-charge is maintained in the 100% to 75% range), then the system may not detect that the power source is aging if only a single buffer threshold such as buffer threshold 413 is used for adjusting the available capacity.

A technical effect of the disclosure is the adjustment of an available capacity of a rechargeable power source. Another technical effect of the disclosure is the increase of a usable capacity of a battery. For example, by adjusting the available capacity over the useful life of the power source to optimize the usable capacity of the power source, the initial capacity can be set to a greater value. Yet another technical effect of the disclosure is the display of a state-of-charge for a battery wherein the state-of-charge is based on an available capacity of the battery, the available capacity of the battery lower than the actual available capacity of the battery.

In one embodiment, a method comprises controlling an x-ray source to generate an x-ray exposure, measuring a voltage of a power supply coupled to the x-ray source during the x-ray exposure, and adjusting an available capacity of the power supply based on the voltage.

In a first example of the method, adjusting the available capacity of the power supply based on the voltage comprises adjusting the available capacity of the power supply responsive to the voltage below a threshold. In a second example of the method optionally including the first example, the threshold is dependent on a state-of-charge of the power supply. In a third example of the method optionally including one or more of the first and second examples, the threshold comprises a plurality of thresholds, each threshold of the plurality of thresholds corresponding to a different range in a plurality of ranges of the state-of-charge of the power supply. In a fourth example of the method optionally including one or more of the first through third examples, the threshold defines a margin above an error-free threshold, the error-free threshold comprising a voltage value below which errors occur in the x-ray exposure. In a fifth example of the method optionally including one or more of the first through fourth examples, adjusting the available capacity of the power supply comprises decreasing an available capacity of the power supply. In a sixth example of the method optionally including one or more of the first through fifth examples, the available capacity of the power supply is decreased by a predetermined amount. In a seventh example of the method optionally including one or more of the first through sixth examples, the available capacity is decreased by an amount, the amount based on the voltage. In an eighth example of the method optionally including one or more of the first through seventh examples, the method further comprises updating a state-of-charge of the power supply based on the adjusted available capacity, and displaying the updated state-of-charge of the power supply.

In another embodiment, an imaging system comprises a rechargeable power supply, an x-ray source electrically coupled to the rechargeable power supply, control circuitry for controlling the x-ray source, and a display configured to display a state-of-charge of the rechargeable power supply, wherein the control circuitry is configured with instructions in non-transitory memory that when executed cause the control circuitry to: measure a voltage of the rechargeable power supply while controlling the x-ray source during an x-ray exposure; adjust an available capacity of the rechargeable power supply based on the measured voltage; and update the state-of-charge based on the adjusted available capacity.

In a first example of the imaging system, adjusting the available capacity of the rechargeable power supply based on the measured voltage comprises decreasing the available capacity of the rechargeable power supply responsive to the measured voltage below a threshold. In a second example of the imaging system optionally including the first example, the threshold depends on the state-of-charge of the rechargeable power supply. In a third example of the imaging system optionally including one or more of the first and second examples, the threshold depends on the available capacity. In a fourth example of the imaging system optionally including one or more of the first through third examples, the control circuitry is further configured with instructions in the non-transitory memory that when executed cause the control circuitry to measure the state-of-charge of the rechargeable power supply based on current integration. In a fifth example of the imaging system optionally including one or more of the first through fourth examples, the control circuitry is further configured with instructions in the non-transitory memory that when executed cause the control circuitry to output, via the display, an indication that the rechargeable power supply should be replaced responsive to adjusting the available capacity to a final available capacity. In a sixth example of the imaging system optionally including one or more of the first through fifth examples, the imaging system comprises a portable imaging system. For example, the imaging system may further comprise a portable cart, wherein the rechargeable power supply and/or the x-ray source are disposed on the portable cart. As another example, the imaging system may comprise a portable/movable imaging system, and thus may include wheels, but the imaging system may not be configured as a portable cart. In a seventh example of the imaging system optionally including one or more of the first through fifth examples, the imaging system comprises a stationary imaging system.

In yet another embodiment, a method comprises measuring a voltage of a rechargeable power supply coupled to an x-ray source during an x-ray exposure, reducing an available capacity of the rechargeable power supply based on the voltage, updating a state-of-charge of the rechargeable power supply based on the reduced available capacity, and displaying the updated state-of-charge of the rechargeable power supply.

In a first example of the method, an initial available capacity of the rechargeable power supply comprises a percentage of a full rated capacity of the rechargeable power supply, the percentage less than 100%. In a second example of the method optionally including the first example, a final available capacity of the rechargeable power supply comprises a percentage of the full rated capacity of the rechargeable power supply, the percentage greater than 0%. In a third example of the method optionally including one or more of the first and second examples, the method further comprises displaying a notification to service the rechargeable power supply responsive to reducing the available capacity to the final available capacity. In a fourth example of the method optionally including one or more of the first through third examples, reducing the available capacity of the rechargeable power supply based on the voltage comprises reducing the available capacity of the rechargeable power supply responsive to the voltage below a threshold.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
controlling an x-ray source to generate an x-ray exposure;
measuring a voltage of a power supply coupled to the x-ray source during the x-ray exposure; and
adjusting an available capacity of the power supply based on the voltage.

2. The method of claim 1, wherein adjusting the available capacity of the power supply based on the voltage comprises adjusting the available capacity of the power supply responsive to the voltage below a threshold.

3. The method of claim 2, wherein the threshold is dependent on a state-of-charge of the power supply.

4. The method of claim 3, wherein the threshold comprises a plurality of thresholds, each threshold of the plurality of thresholds corresponding to a different range in a plurality of ranges of the state-of-charge of the power supply.

5. The method of claim 2, wherein the threshold defines a margin above an error-free threshold, the error-free threshold comprising a voltage value below which errors occur in the x-ray exposure.

6. The method of claim 1, wherein adjusting the available capacity of the power supply comprises decreasing an available capacity of the power supply.

7. The method of claim 6, wherein the available capacity of the power supply is decreased by a predetermined amount, or by an amount based on the voltage.

8. The method of claim 1, wherein the power supply comprises one or more batteries.

9. The method of claim 1, further comprising updating a state-of-charge of the power supply based on the adjusted available capacity, and displaying the updated state-of-charge of the power supply.

10. An imaging system, comprising:
a rechargeable power supply;
an x-ray source electrically coupled to the rechargeable power supply;
control circuitry for controlling the x-ray source; and
a display configured to display a state-of-charge of the rechargeable power supply;
wherein the control circuitry is configured with instructions in non-transitory memory that when executed cause the control circuitry to:
measure a voltage of the rechargeable power supply while controlling the x-ray source during an x-ray exposure;
adjust an available capacity of the rechargeable power supply based on the measured voltage; and
update the state-of-charge based on the adjusted available capacity.

11. The imaging system of claim 10, wherein adjusting the available capacity of the rechargeable power supply based on the measured voltage comprises decreasing the available capacity of the rechargeable power supply responsive to the measured voltage below a threshold.

12. The imaging system of claim 11, wherein the threshold depends on the state-of-charge of the rechargeable power supply.

13. The imaging system of claim 11, wherein the threshold depends on the available capacity.

14. The imaging system of claim 10, wherein the control circuitry is further configured with instructions in the non-transitory memory that when executed cause the control circuitry to measure the state-of-charge of the rechargeable power supply based on current integration.

15. The imaging system of claim 10, wherein the control circuitry is further configured with instructions in the non-transitory memory that when executed cause the control circuitry to output, via the display, an indication that the rechargeable power supply should be replaced responsive to adjusting the available capacity to a final available capacity.

16. The imaging system of claim 10, wherein the imaging system is a portable imaging system.

17. A method, comprising:
measuring a voltage of a rechargeable power supply coupled to an x-ray source during an x-ray exposure;
reducing an available capacity of the rechargeable power supply based on the voltage;
updating a state-of-charge of the rechargeable power supply based on the reduced available capacity; and
displaying the updated state-of-charge of the rechargeable power supply.

18. The method of claim 17, wherein an initial available capacity of the rechargeable power supply comprises a first percentage of a full rated capacity of the rechargeable power supply, the first percentage less than 100%, and wherein a final available capacity of the rechargeable power supply comprises a second percentage of the full rated capacity of the rechargeable power supply, the second percentage greater than 0%.

19. The method of claim 18, further comprising displaying a notification to service the rechargeable power supply responsive to reducing the available capacity to the final available capacity.

20. The method of claim 17, wherein reducing the available capacity of the rechargeable power supply based on the voltage comprises reducing the available capacity of the rechargeable power supply responsive to the voltage below a threshold.

* * * * *